United States Patent
Kiyose et al.

(10) Patent No.: US 10,716,541 B2
(45) Date of Patent: Jul. 21, 2020

(54) ULTRASONIC DEVICE, ULTRASONIC MODULE, ELECTRONIC APPARATUS, AND ULTRASONIC MEASUREMENT APPARATUS

(71) Applicant: Seiko Epson Corporation, Tokyo (JP)

(72) Inventors: Kanechika Kiyose, Matsumoto (JP); Nobuaki Hashimoto, Suwa (JP)

(73) Assignee: Seiko Epson Corporation (JP)

( * ) Notice: Subject to any disclaimer, the term of this patent is extended or adjusted under 35 U.S.C. 154(b) by 721 days.

(21) Appl. No.: 15/209,046

(22) Filed: Jul. 13, 2016

(65) Prior Publication Data

US 2017/0020484 A1     Jan. 26, 2017

(30) Foreign Application Priority Data

Jul. 24, 2015  (JP) ................................. 2015-147109

(51) Int. Cl.
| | | |
|---|---|---|
| *A61B 8/00* | (2006.01) | |
| *A61B 8/14* | (2006.01) | |
| *H01L 41/083* | (2006.01) | |
| *H01L 41/047* | (2006.01) | |
| *H01L 41/08* | (2006.01) | |
| *G01N 29/34* | (2006.01) | |

(Continued)

(52) U.S. Cl.
CPC .......... *A61B 8/4494* (2013.01); *A61B 8/4427* (2013.01); *A61B 8/54* (2013.01); *G01N 29/22* (2013.01); *G01N 29/34* (2013.01); *B06B 1/0629* (2013.01); *B06B 2201/55* (2013.01); *B06B 2201/76* (2013.01)

(58) Field of Classification Search
CPC ....... A61B 8/4494; A61B 8/4427; A61B 8/54; G01N 29/22; G01N 29/34; B06B 1/0629; B06B 2201/55; B06B 2201/76
See application file for complete search history.

(56) References Cited

U.S. PATENT DOCUMENTS

| | | | |
|---|---|---|---|
| 9,554,775 B2 * | 1/2017 | Nakamura | ............ B06B 1/0622 |
| 10,424,720 B2 * | 9/2019 | Kiyose | ................ H01L 41/0475 |
| 2003/0102777 A1 | 6/2003 | Kuniyasu et al. | |

(Continued)

FOREIGN PATENT DOCUMENTS

| | | | | |
|---|---|---|---|---|
| CN | 104 771 190 A | | 7/2015 | |
| CN | 104771190 A | * | 7/2015 | ........... B06B 1/0292 |

(Continued)

*Primary Examiner* — Daniel Pihulic

(74) *Attorney, Agent, or Firm* — Harness, Dickey & Pierce, P.L.C.

(57) ABSTRACT

An ultrasonic device includes an element substrate, an ultrasonic transducer array disposed on a rear surface of the element substrate, and having a plurality of ultrasonic transducers arranged in an array, an electrode line connected to the ultrasonic transducer on the rear surface of the element substrate, and drawn to a terminal region located outside the ultrasonic transducer array in a planar view of the element substrate viewed from a normal direction, a sealing plate bonded to the rear surface side of the element substrate, and a through electrode penetrating the sealing plate in a thickness direction and connected to an electrode pad of the electrode line at a position, which is located outside a region opposed to the ultrasonic transducer array of the sealing plate and is opposed to the electrode pad.

7 Claims, 8 Drawing Sheets

(51) Int. Cl.
*G01N 29/22* (2006.01)
*B06B 1/06* (2006.01)

(56) References Cited

U.S. PATENT DOCUMENTS

| | | |
|---|---|---|
| 2005/0140248 A1 | 6/2005 | Kuniyasu et al. |
| 2008/0089181 A1 | 4/2008 | Adachi et al. |
| 2014/0296715 A1 | 10/2014 | Kiyose et al. |
| 2015/0198564 A1 | 7/2015 | Endo |
| 2017/0020484 A1* | 1/2017 | Kiyose ............... A61B 8/54 |
| 2017/0031024 A1* | 2/2017 | Kiyose ............. B06B 1/0629 |

FOREIGN PATENT DOCUMENTS

| | | |
|---|---|---|
| JP | 2003-235098 A | 8/2003 |
| JP | 2008-118631 A | 5/2008 |
| JP | 2011-255024 A | 12/2011 |
| JP | 2014-209728 A | 11/2014 |

\* cited by examiner

ULTRASONIC DEVICE, ULTRASONIC MODULE, ELECTRONIC APPARATUS, AND ULTRASONIC MEASUREMENT APPARATUS

BACKGROUND

1. Technical Field

The present invention relates to an ultrasonic device, an ultrasonic module, an electronic apparatus, and an ultrasonic measurement apparatus.

2. Related Art

In the past, there has been known an ultrasonic device provided with an element substrate having ultrasonic vibrators each vibrating in accordance with a signal input to output an ultrasonic wave, and first terminal parts respectively connected to the ultrasonic vibrators, and a wiring board having second terminal parts electrically connected to respective terminals of the element substrate (see, e.g., JP-A-2014-209728 (Document 1)).

In the ultrasonic device described in Document 1, the element substrate having opening parts is provided with a support film for covering the opening parts, and ultrasonic transducers each having a lower-part electrode, a piezoelectric film, and an upper-part electrode stacked on one another are disposed on the support film. Further, on the surface of the opening parts of the element substrate, there is disposed a back plate (a reinforcing plate) for suppressing a back wave. In such an ultrasonic device, reduction in thickness and miniaturization can be realized compared to the ultrasonic device using a bulk-type piezoelectric body.

Incidentally, in the case of inspecting, for example, a part in a living body using an ultrasonic device, a liquid such as a gel is applied to the ultrasonic emission side of the ultrasonic device so that air does not intervene between the ultrasonic device and the living body. However, if the ultrasonic transducers and electrodes are disposed on the element side surfaces of the element substrate as in Document 1 described above, a liquid such as a water droplet adheres to become a cause of a false operation or a failure. Although it is also possible to adopt a configuration of providing a protective film for achieving a waterproof property, if such a protective film is disposed on the emission side of the ultrasonic wave, the ultrasonic wave is reflected by the protective film due to the difference in ultrasonic impedance, and an accurate inspection using the ultrasonic wave cannot be performed.

Further, in such a configuration as described in Document 1, it is possible to adopt a configuration of outputting the ultrasonic wave from the surface on the opening part side of the element substrate. In such a configuration, it is possible to sufficiently ensure the waterproof property with respect to the electrode lines connected to the piezoelectric elements (the lower-part electrodes, the piezoelectric films, and the upper-part electrodes) and the electrodes.

In contrast, in the ultrasonic transducers each shaped like a thin film, since the thin element substrate is used, there is a necessity of bonding a reinforcing plate (a sealing plate) to thereby reinforce the element substrate. Here, since it is not possible to adopt a configuration of disposing the reinforcing plate on a transmission/reception surface for the ultrasonic wave out of the element substrate (the reinforcing plate becomes an obstacle to the ultrasonic transmission/reception), it results that the reinforcing plate is disposed on the rear surface side of the element substrate. However, as described above, in the configuration in which the piezoelectric elements and the electrode lines are disposed on the rear surface side of the element substrate, it results that the terminal parts for achieving the connection to the wiring board are also disposed on the rear surface side. FIG. 7 shows an example of a configuration of a related-art ultrasonic device. As shown in FIG. 7, in such a configuration described above, it results that flexible printed circuits (FPC) 71 are connected to the terminal parts (electrode pads 414P) of the element substrate 41, and the FPC 71 are drawn through the opening 73 provided to the reinforcing plate (the sealing plate 72) and are connected to wiring terminal parts provided to the wiring board. In this case, there is a possibility that the element substrate 41 is lifted or tilted due to the reactive force of the FPC 71, and the control of the ultrasonic transmission/reception direction becomes difficult. Further, there is also a possibility that the FPC is broken at a corner part of the opening 73 of the reinforcing plate 72, and the wiring reliability is degraded.

SUMMARY

An advantage of some aspects of the invention is to provide an ultrasonic device, an ultrasonic module, an electronic apparatus, and an ultrasonic measurement apparatus high in wiring reliability, and each capable of accurate transmission/reception control.

An ultrasonic device according to an application example of the invention includes an element substrate having a first surface and a second surface located on an opposite side to the first surface, an ultrasonic transducer array disposed on the first surface of the element substrate, and having a plurality of ultrasonic transducers arranged in an array, at least one electrode line connected to the ultrasonic transducer in the first surface of the element substrate, and drawn outside the ultrasonic transducer array in a planar view of the element substrate viewed from a normal direction, a sealing plate bonded to the first surface of the element substrate, and at least one through electrode, which is disposed so as to penetrate the sealing plate in a thickness direction and is connected to a part of the electrode line at a position, which is outside an array opposed region opposed to the ultrasonic transducer array of the sealing plate in the planar view and is opposed to the part of the electrode line.

In this application example, the electrode line is disposed on the first surface of the element substrate on which the ultrasonic transducer array is disposed, and the ultrasonic wave is emitted from the second surface on the opposite side to the first surface. Further, the sealing plate is disposed so as to be opposed to the first surface of the element substrate, and the through electrode to electrically connected to the electrode line disposed on the first surface of the element substrate is disposed outside the array opposed region opposed to the ultrasonic transducer array of the sealing plate.

In such a configuration, in the case of using the ultrasonic device for, for example, an ultrasonic probe used for the inspection of the living body, even in the case in which a liquid such as a gel intervenes between the ultrasonic probe and the living body, and the liquid infiltrates in the ultrasonic probe, the liquid does not adhere to the ultrasonic transducer array or the electrode lines, and thus a failure and a malfunction can be inhibited.

Further, even in the case in which the element substrate is thin, the strength of the element substrate can be reinforced by the sealing plate, and breakage due to an impact or the like can be inhibited.

Incidentally, when disposing such a sealing plate on the first surface side of the element substrate, if the connection with the FPC is performed in order to electrically connect the electrode line of the element substrate and the wiring board to each other, there arises a problem such as a lift of the element substrate or breaking of the FPC. In contrast, in this application example, the through electrode is disposed outside the array opposed region of the sealing plate to connect the electrode line drawn to the outside of the array region of the element substrate and the through electrode to each other. Thus, the variation in transmission/reception direction of the ultrasonic wave due to the lift of the element substrate is suppressed, and thus, more accurate transmission/reception control of the ultrasonic wave can be performed. Further, since there is adopted the configuration of using the through electrode, the problem such as breaking of the wiring does not occur. Moreover, since the electrode line disposed on the element substrate is electrically connected to the through electrode, and the through electrode penetrates the sealing plate to the opposite side to the element substrate, one end of the through electrode located on the opposite side to the element substrate can be directly bonded to a desired position of the wiring board with solder (so-called face-down mounting), the operation process in the mounting stage of the ultrasonic device can be simplified, and thus, the manufacturing efficiency can be enhanced.

Here, it is also possible to adopt a configuration of disposing the through electrode inside the array opposed region. However, in this case, it is necessary to align the through electrode with the electrode line drawn between the ultrasonic transducers to have contact with each other. Since the distance dimension between the ultrasonic transducers is minute, it is difficult to connect the through electrode to the electrode line between the ultrasonic transducers, and the manufacturing efficiency also becomes worse.

Further, in the configuration of vibrating the vibrating film with the ultrasonic transducer array, if the ultrasonic transducer array and the sealing plate are bonded to each other, it results that the vibration of the vibrating film is hindered. Therefore, it is necessary to provide a predetermined gap between the ultrasonic transducer array and the sealing plate. Therefore, in the case of disposing the through electrode in the array opposed region, it is necessary to form a through electrode projecting toward the first surface as much as a gap dimension between the ultrasonic transducer array and the sealing plate, and at the same time, to connect the through electrode and the electrode line to each other while the vibrating film is vibrating. However, there is a possibility that the through electrode and the electrode line are broken due to the vibration when the vibrating film vibrates, and thus, sufficient reliability cannot be ensured.

In contrast, by adopting the configuration of connecting the through electrode to the electrode line located outside the array region as in this application example, it is possible to reliably and easily connect the through electrode to each of the ultrasonic transducers, and an improvement in the manufacturing efficiency and an improvement in reliability can be achieved.

In the ultrasonic device according to the application example, it is preferable that the element substrate is provided with opening parts corresponding respectively to the ultrasonic transducers, and a vibrating film closing the opening parts.

In the application example with this configuration, the element substrate is provided with the opening parts corresponding respectively to the ultrasonic transducers and the vibrating film for closing the opening parts, and the ultrasonic transducers are disposed on the first surface side of the vibrating film.

According to such a configuration, by driving the ultrasonic transducers to vibrate the vibrating film, it is possible to emit the ultrasonic wave, and further, by detecting the deformation of the ultrasonic transducers due to the vibration of the vibrating film, it is possible to receive the ultrasonic wave. On this occasion, since the electrode line is disposed on the first surface side of the vibrating film as described above, a water droplet or the like having infiltrated from the transmission/reception surface of the ultrasonic wave dose not adhere to the ultrasonic transducers or the electrode line, and thus the waterproof property can be ensured.

In the ultrasonic device according to the application example, it is preferable that the vibrating film closes the first surface side of the opening parts.

In the application example with this configuration, the vibrating film closes the first surface side of the opening parts. Therefore, by providing the vibrating film on the first surface side of the opening parts, the first surface side of the element substrate has a flat shape. Therefore, since the electrode line drawn from the ultrasonic transducers is not disposed on the uneven surface of the opening parts, breaking of the electrode line can be inhibited, and the reliability can be enhanced. Further, since the ultrasonic transducers and the electrode lines are formed on the vibrating film having the flat shape, the manufacturing efficiency is also enhanced.

Further, in such a configuration, by driving the ultrasonic transducers, it is possible to emit the ultrasonic wave on the opening part side of the element substrate, and it is also possible to receive the ultrasonic wave entering the opening part side.

In the ultrasonic device according to the application example, it is preferable that the ultrasonic transducers are each a laminated body having a first electrode, a piezoelectric film, and a second electrode stacked in sequence, the electrode line is provided with a first electrode line connected to the first electrode, and a second electrode line connected to the second electrode, and the through electrode is provided with a first through electrode connected to the first electrode line, and a second through electrode connected to the second electrode line.

In the application example with this configuration, the ultrasonic transducers are each configured including the first electrode, the piezoelectric film, and the second electrode stacked one another. In other words, the ultrasonic transducers of the application example are each formed of the laminated body shaped like a film, and thus, the height reduction of the ultrasonic device can be realized.

Further, the electrode lines are disposed respectively to the first electrode and the second electrode, and the electrode lines are respectively connected to the through electrodes. In such a configuration, it is also possible to individually input signals to the first electrode and the second electrode of each of the ultrasonic transducers, and it is possible to make the ultrasonic transducer array function as a two-dimensional ultrasonic transducer array.

In the ultrasonic device according to the application example, it is preferable that the ultrasonic transducer array has an array structure in which a plurality of the ultrasonic transducers arranged along a first direction constitutes an ultrasonic transducer group, and a plurality of the ultrasonic transducer groups is arranged along a second direction crossing the first direction, the first electrode lines connected respectively to the ultrasonic transducers belonging to the ultrasonic transducer group are electrically connected to each other, and the second electrode lines connected respectively to the ultrasonic transducers belonging to the ultrasonic transducer group are electrically connected to each other.

In the application example with this configuration, the ultrasonic transducer array has the array structure in which the plurality of ultrasonic transducers arranged in the first direction constitutes one ultrasonic transducer group, and the plurality of ultrasonic transducer groups are arranged along the second direction. Thus, the ultrasonic transducer array can be driven as a one-dimensional array. On this occasion, since the plurality of ultrasonic transducers constitutes the ultrasonic transducer group, it is possible to achieve an improvement in sound pressure of the transmitted ultrasonic wave and an improvement in reception accuracy of the received ultrasonic wave compared to the case of, for example, performing the transmission/reception of the ultrasonic wave with a single ultrasonic transducer.

Further, since the first electrodes of the respective ultrasonic transducers belonging to the ultrasonic transducer group are connected to each other, and the second electrodes of the respective ultrasonic transducers belonging to the ultrasonic transducer group are connected to each other, the number of the through electrodes to one ultrasonic transducer group can be reduced. For example, if the through electrode corresponding to the first electrode and the through electrode corresponding to the second electrode are disposed to one ultrasonic transducer group, it is possible to drive the ultrasonic transducer group. Further, since the number of the through electrodes can be reduced compared to the case of disposing the through electrodes respectively to the ultrasonic transducers, the through electrodes to be disposed to the sealing plate can be reduced, and the decrease in strength of the sealing plate can be suppressed accordingly.

An ultrasonic module according to an application example of the invention includes an element substrate having a first surface and a second surface located on an opposite side to the first surface, an ultrasonic transducer array disposed on the first surface of the element substrate, and having a plurality of ultrasonic transducers arranged in an array, at least one electrode line connected to the ultrasonic transducer in the first surface of the element substrate, and drawn outside the ultrasonic transducer array in a planar view of the element substrate viewed from a normal direction, a sealing plate bonded to the first surface of the element substrate, at least one through electrode, which is disposed so as to penetrate the sealing plate in a thickness direction and is connected to apart of the electrode line at a position, which is outside an array opposed region opposed to the ultrasonic transducer array of the sealing plate in the planar view and is opposed to the part of the electrode line, and a wiring board provided with at least one terminal part to be connected to the through electrode.

In the ultrasonic module according to this application example, since the first surface side of the element substrate, on which the ultrasonic transducers and the electrode lines are disposed, is the opposite side to the transmission/reception surface of the ultrasonic wave similarly to the ultrasonic device described above, a sufficient waterproof property can be ensured. Further, even if the ultrasonic transducers are disposed on the first surface, by disposing the sealing plate, the strength of the element substrate can sufficiently be ensured, and at the same time, the cross talk can be suppressed. Further, since the through electrodes are disposed outside the array opposed region, the ultrasonic device can easily be mounted on the wiring board using the face-down mounting, and it is possible to achieve an improvement in manufacturing efficiency and an improvement in reliability.

An electronic apparatus according to an application example of the invention includes an element substrate having a first surface and a second surface located on an opposite side to the first surface, an ultrasonic transducer array disposed on the first surface of the element substrate, and having a plurality of ultrasonic transducers arranged in an array, at least one electrode line connected to the ultrasonic transducer in the first surface of the element substrate, and drawn outside the ultrasonic transducer array in a planar view of the element substrate viewed from a normal direction, a sealing plate bonded to the first surface of the element substrate, at least one through electrode, which is disposed so as to penetrate the sealing plate in a thickness direction and is connected to apart of the electrode line at a position, which is outside an array opposed region opposed to the ultrasonic transducer array of the sealing plate in the planar view and is opposed to the part of the electrode line, a wiring board provided with at least one terminal part to be connected to the through electrode, and a control section adapted to control the ultrasonic transducers.

In the electronic apparatus according to this application example, since the first surface side of the element substrate, on which the ultrasonic transducers and the electrode lines are disposed, is the opposite side to the transmission/reception surface of the ultrasonic wave similarly to the ultrasonic device and the ultrasonic module described above, a sufficient waterproof property can be ensured. Further, even if the ultrasonic transducers are disposed on the first surface, by disposing the sealing plate, the strength of the element substrate can sufficiently be ensured, and at the same time, the cross talk can be suppressed. Further, since the through electrodes are disposed outside the array opposed region, the ultrasonic device can easily be mounted on the wiring board using the face-down mounting, and it is possible to achieve an improvement in manufacturing efficiency and an improvement in reliability.

Therefore, in the electronic apparatus incorporating such an ultrasonic device or such an ultrasonic module, the functions and the advantages described above can be obtained, and accurate transmission/reception of the ultrasonic wave can be performed.

An ultrasonic measurement apparatus according to an application example of the invention includes an element substrate having a first surface and a second surface located on an opposite side to the first surface, an ultrasonic transducer array disposed on the first surface of the element substrate, and having a plurality of ultrasonic transducers arranged in an array, at least one electrode line connected to the ultrasonic transducer in the first surface of the element substrate, and drawn outside the ultrasonic transducer array in a planar view of the element substrate viewed from a normal direction, a sealing plate bonded to the first surface of the element substrate, at least one through electrode, which is disposed so as to penetrate the sealing plate in a thickness direction and is connected to a part of the electrode line at a position, which is outside an array opposed region opposed to the ultrasonic transducer array of the sealing plate in the planar view and is opposed to the part of the electrode line, a wiring board provided with at least one terminal part to be connected to the through electrode, and a measurement control section adapted to control transmission of an ultrasonic wave from the ultrasonic transducer array and reception of the ultrasonic wave reflected to measure a measurement target based on transmission/reception timing of the ultrasonic wave. It should be noted that the measurement by the measurement control section also includes, for example, those measuring the flow rate of a measurement target fluid in addition to a surface shape and a cross-sectional shape of the measurement target.

In the ultrasonic measurement apparatus according to this application example, since the first surface side of the element substrate, on which the ultrasonic transducers and the electrode lines are disposed, is the opposite side to the transmission/reception surface of the ultrasonic wave similarly to the ultrasonic device and the ultrasonic module described above, a sufficient waterproof property can be ensured. Further, even if the ultrasonic transducers are disposed on the first surface, by disposing the sealing plate, the strength of the element substrate can sufficiently be ensured, and at the same time, the cross talk can be suppressed. Further, since the through electrodes are disposed outside the array opposed region, the ultrasonic device can easily be mounted on the wiring board using the face-down mounting, and it is possible to achieve an improvement in manufacturing efficiency and an improvement in reliability.

Therefore, in the ultrasonic measurement apparatus incorporating such an ultrasonic device or such an ultrasonic module, the functions and the advantages described above can be obtained, and accurate transmission/reception of the ultrasonic wave can be performed, and further, an accurate measurement process of the object using the ultrasonic wave can be performed.

BRIEF DESCRIPTION OF THE DRAWINGS

The invention will be described with reference to the accompanying drawings, wherein like numbers reference like elements.

DESCRIPTION OF EXEMPLARY EMBODIMENTS

An ultrasonic measurement apparatus as an electronic apparatus of an embodiment according to the invention will hereinafter be described with reference to the accompanying drawings.

Configuration of Ultrasonic Measurement Apparatus 1

Figure 1:
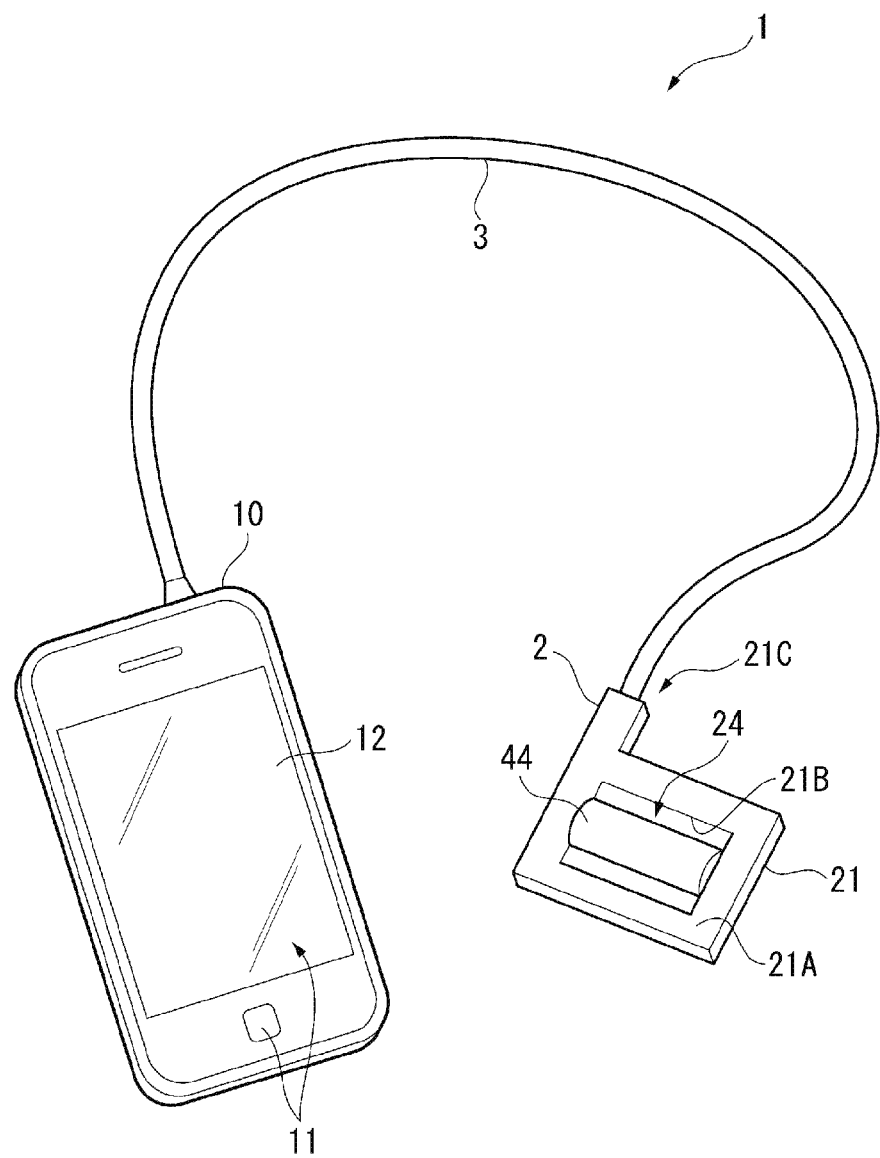
FIG. 1 is a perspective view showing a general configuration of an ultrasonic measurement apparatus according to an embodiment of the invention.
Figure 2:
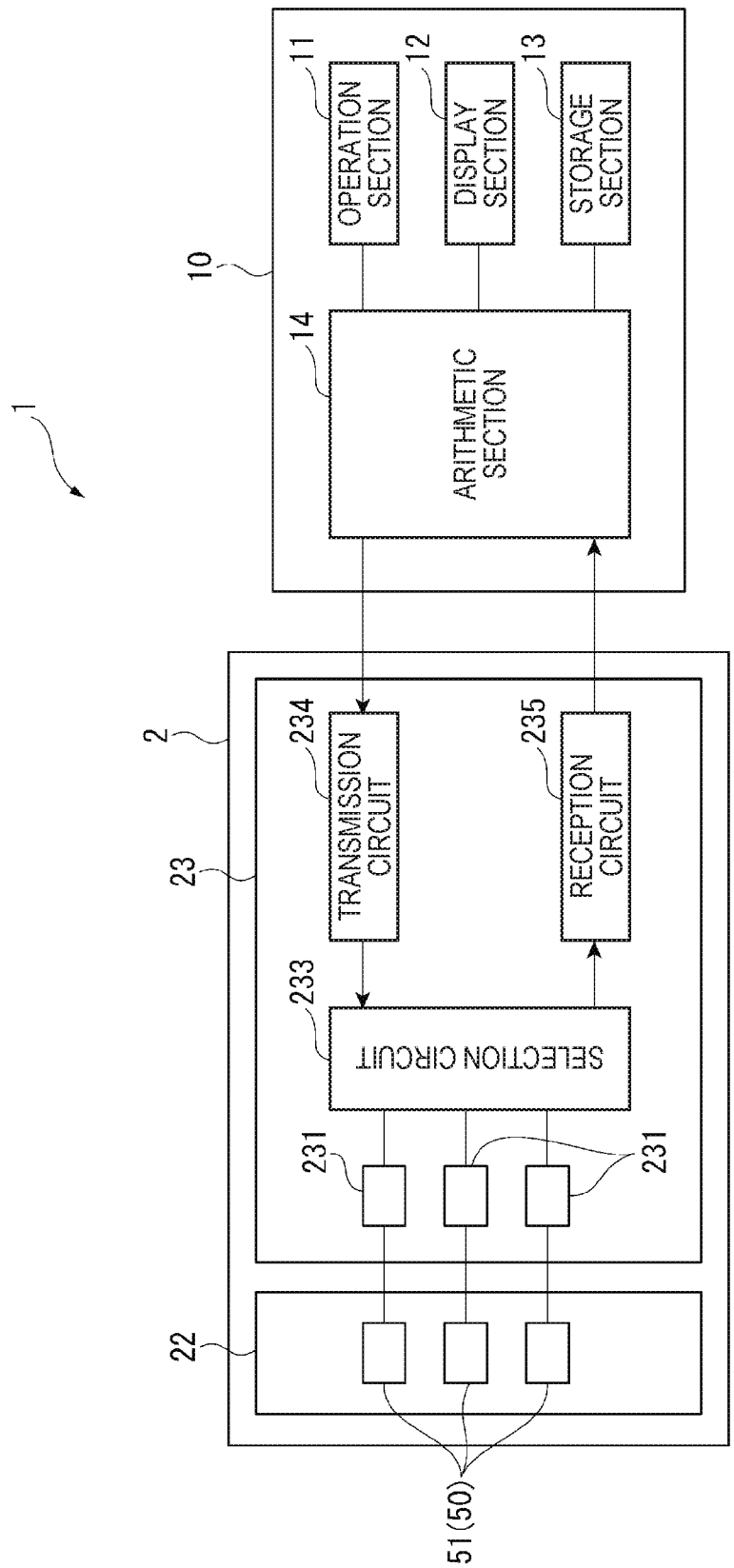
FIG. 2 is a block diagram showing a general configuration of the ultrasonic measurement apparatus according to the embodiment.

FIG. 1 is a perspective view showing a general configuration of the ultrasonic measurement apparatus 1 according to the present embodiment. FIG. 2 is a block diagram showing a general configuration of the ultrasonic measurement apparatus 1.

As shown in FIG. 1, the ultrasonic measurement apparatus 1 according to the present embodiment is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) with the ultrasonic probe 2 having contact with a surface of the living body. Further, the ultrasonic measurement apparatus 1 receives the ultrasonic wave reflected by apart in the living body using the ultrasonic probe 2, and then, for example, obtains an internal tomographic image in the living body and measures the state (e.g., blood pressure and blood flow) of the part in the living body based on the received signal.

Configuration of Ultrasonic Probe 2

Figure 3:
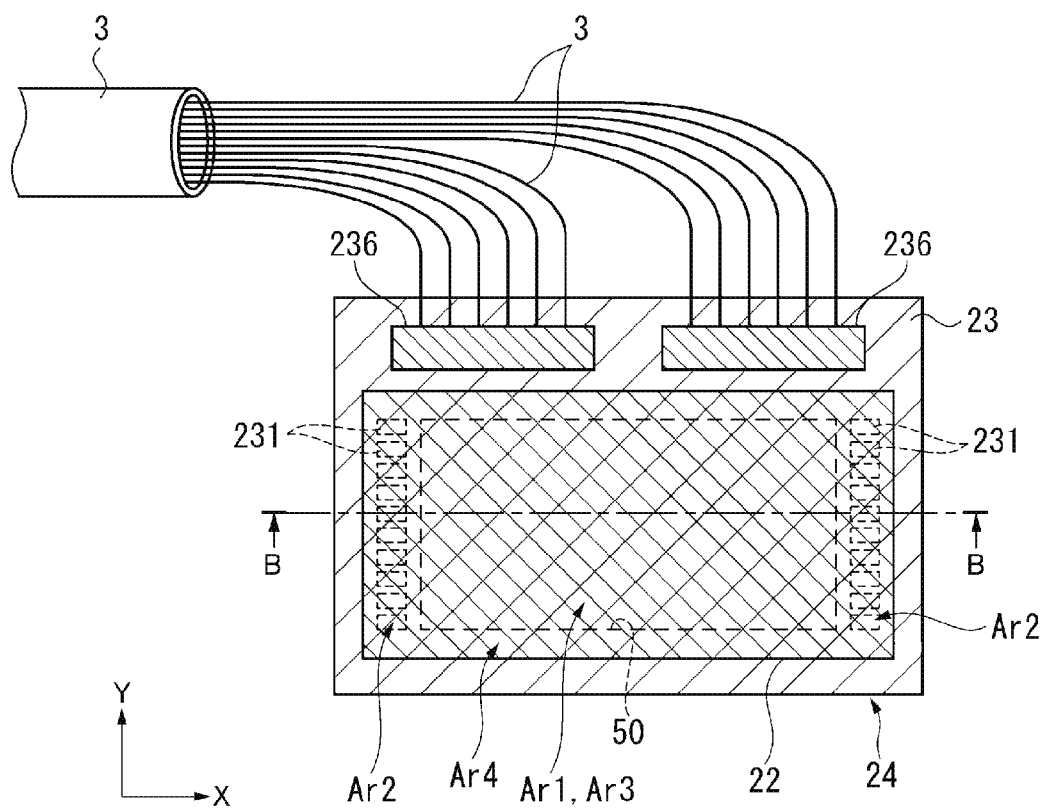
FIG. 3 is a plan view showing a general configuration of an ultrasonic sensor in an ultrasonic probe of the embodiment.

FIG. 3 is a plan view showing a general configuration of an ultrasonic sensor 24 in the ultrasonic probe 2.

The ultrasonic probe 2 is provided with a housing 21, an ultrasonic device 22 disposed inside the housing 21, and a wiring board 23 provided with a driver circuit for controlling the ultrasonic device 22 and so on. It should be noted that the ultrasonic sensor 24 is constituted by the ultrasonic device 22 and the wiring board 23, and the ultrasonic sensor 24 constitutes an ultrasonic module according to the invention.

As shown in FIG. 1, the housing 21 is formed to have a box-like shape having a rectangular planar shape, and on one surface (a sensor surface 21A) perpendicular to the thickness direction, there is disposed a sensor window 21B, and a part of the ultrasonic device 22 is exposed therefrom. Further, in a part (a side surface in the example shown in FIG. 1) of the housing 21, there is disposed a through hole 21C for the cable 3, and the cable 3 is connected to the wiring board 23 located inside the housing 21 through the through hole 21C. Further, the gap between the cable 3 and the through hole 21C is filled with, for example, a resin material to thereby ensure the waterproof property.

It should be noted that although in the present embodiment, there is shown a configuration example in which the ultrasonic probe 2 and the control device 10 are connected to each other using the cable 3, the configuration is not limited to this example, and it is also possible to, for example, connect the ultrasonic probe 2 and the control device 10 to each other with wireless communication, or dispose a variety of constituents of the control device 10 inside the ultrasonic probe 2.

Configuration of Ultrasonic Device 22

Figure 4:
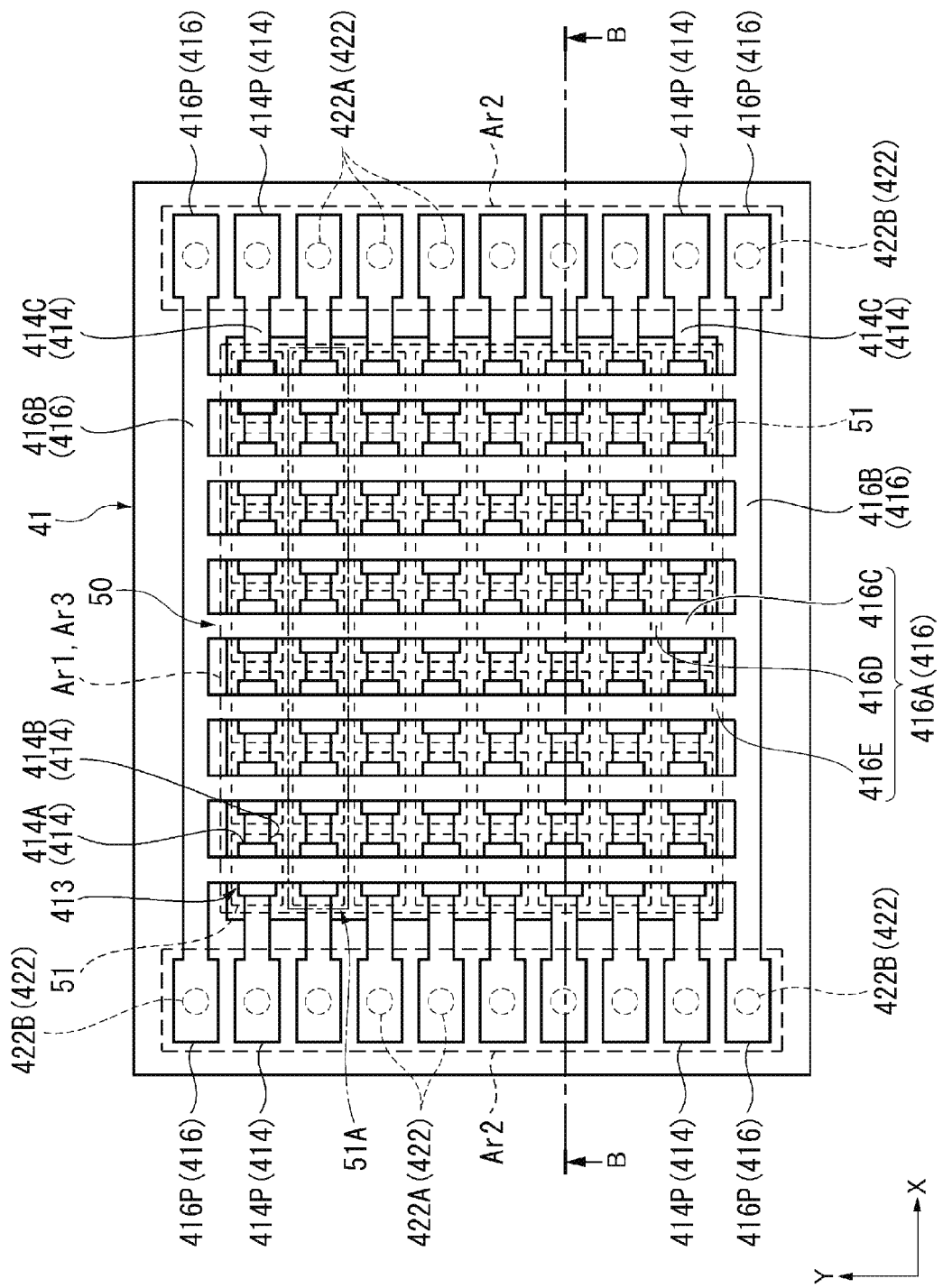
FIG. 4 is a plan view of an element substrate of the ultrasonic sensor according to the embodiment viewed from a sealing plate side.
Figure 5:
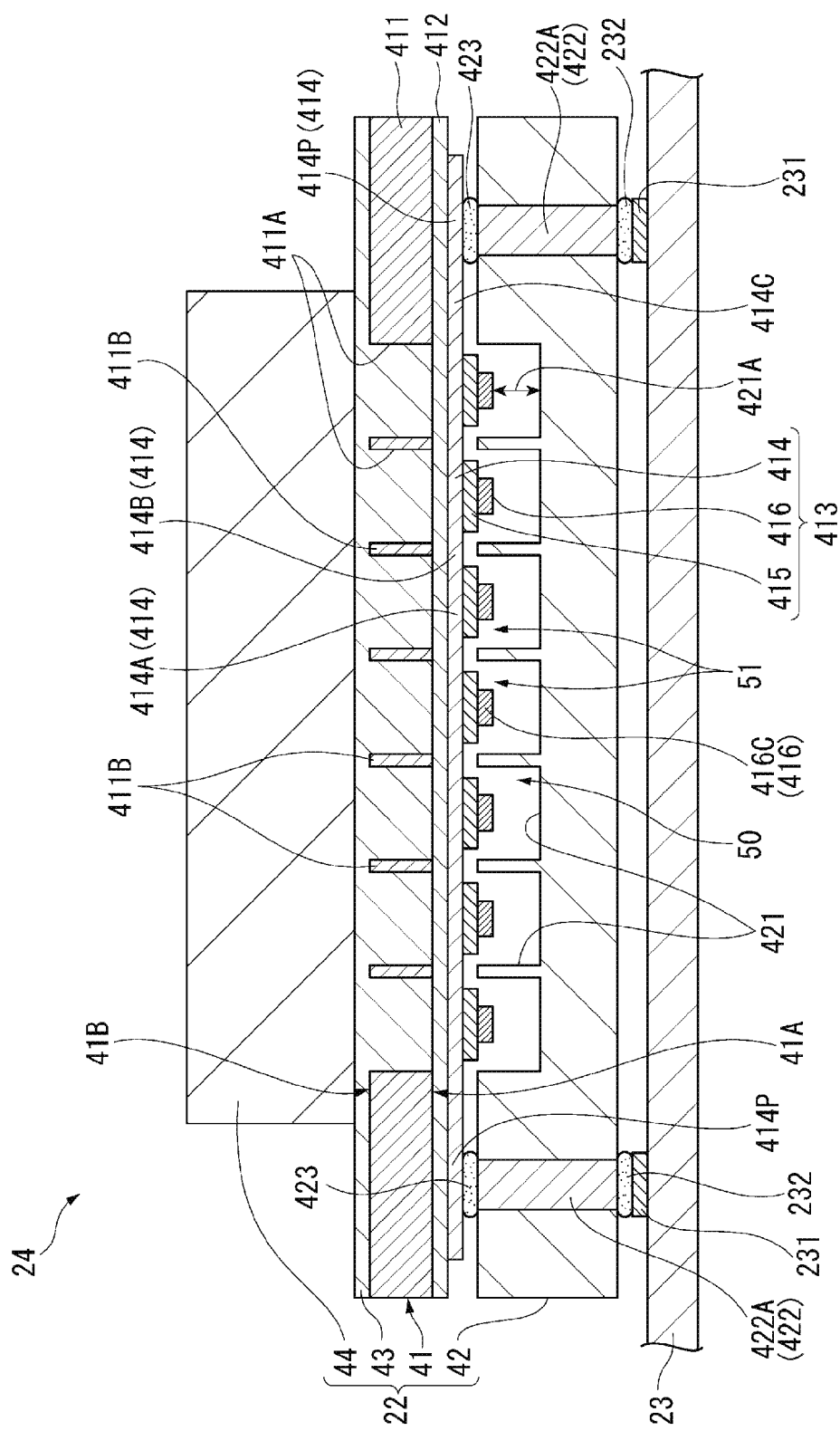
FIG. 5 is a cross-sectional view of the ultrasonic sensor according to the embodiment.

FIG. 4 is a plan view of an element substrate 41 in the ultrasonic device 22 viewed from a sealing plate 42 side. FIG. 5 is a cross-sectional view of the ultrasonic sensor 24 cut along the line B-B shown in FIG. 4.

As shown in FIG. 3 and FIG. 4, the ultrasonic device 22 constituting the ultrasonic sensor 24 is constituted by the element substrate 41, the sealing plate 42, an acoustic matching layer 43 (see FIG. 5), and the acoustic lens 44 (see FIG. 5).

Configuration of Element Substrate 41

As shown in FIG. 5, the element substrate 41 is provided with a substrate main body part 411, a vibrating film 412 stacked on the substrate main body part 411, and piezoelectric elements 413 stacked on the vibrating film 412. Here, in the element substrate 41, a rear surface 41A opposed to the sealing plate 42 forms a first surface according to the invention, and an operation surface 41B on the opposite side to the rear surface 41A forms a second surface according to the invention. Further, the vibrating film 412 and the piezoelectric element 413 constitute the ultrasonic transducer 51 according to the invention.

Further, as shown in FIG. 4, in a planar view of the element substrate 41 viewed from the thickness direction, in a central area of the element substrate 41, there is disposed an ultrasonic transducer array 50 having a plurality of ultrasonic transducers 51 arranged in an array. The area where the ultrasonic transducer array 50 is disposed is hereinafter referred to as an array region Ar1.

The substrate main body part 411 is a semiconductor substrate made of, for example, Si. Inside the array region Ar1 of the substrate main body part 411, there are disposed opening parts 411A corresponding respectively to the ultrasonic transducers 51. Further, the opening parts 411A are closed by the vibrating film 412 disposed on the rear surface 41A side of the substrate main body part 411.

The vibrating film 412 is formed of, for example, $SiO_2$ or a laminated body of $SiO_2$ and $ZrO_2$, and is disposed so as to cover the entire area on the rear surface 41A side of the substrate main body part 411. The thickness dimension of the vibrating film 412 becomes sufficiently small one with respect to the substrate main body part 411. In the case of forming the substrate main body part 411 using Si and forming the vibrating film 412 using $SiO_2$, by performing an oxidation treatment on, for example, the surface on the rear surface 41A side of the substrate main body part 411, it becomes possible to easily form the vibrating film 412 having a desired thickness dimension. Further, in this case, by performing an etching treatment on the substrate main body part 411 using the vibrating film 412 made of $SiO_2$ as an etching stopper, it becomes possible to easily form the opening parts 411A.

Further, as shown in FIG. 5, on the vibrating film 412 closing each of the opening parts 411A, there are disposed the piezoelectric elements 413 each of which is a laminated body of a lower-part electrode 414, a piezoelectric film 415, and an upper-part electrode 416. Here, the vibrating film 412 and the piezoelectric element 413 constitute the ultrasonic transducer 51 according to the invention.

In such an ultrasonic transducer 51, by applying a rectangular-wave voltage having a predetermined frequency between the lower-part electrode 414 and the upper-part electrode 416, it is possible to vibrate the vibrating film 412 in an opening region of each of the opening parts 411A to transmit the ultrasonic wave. Further, when the vibrating film 412 is vibrated by the ultrasonic wave reflected by an object, a potential difference occurs between an upper part and a lower part of the piezoelectric film 415. Therefore, by detecting the potential difference occurring between the lower-part electrode 414 and the upper-part electrode 416, it becomes possible to detect the ultrasonic wave received.

Further, in the present embodiment, as shown in FIG. 4, a plurality of such ultrasonic transducers 51 as described above is arranged in the array region Ar1 of the element substrate 41 along an X direction (a first direction) and a Y direction (a second direction) perpendicular to the X direction.

Here, the lower-part electrode 414 is formed to have a straight-line shape along the X direction. Specifically, the lower-part electrode 414 is constituted by lower-part electrode main bodies 414A, each of which is disposed straddling the plurality of ultrasonic transducers 51 arranged along the X direction, and located between the piezoelectric films 415 and the vibrating film 412, lower-part electrode lines 414B (constituting a part of a first electrode line according to the invention) each connecting the lower-part electrode main bodies 414A adjacent each other, and lower-part terminal electrode lines 414C (constituting a part of the first electrode line according to the invention) each drawn to one of terminal regions Ar2 located outside the array region Ar1. Therefore, in the ultrasonic transducers 51 arranged in the X direction, the lower-part electrodes 414 are in the same potential.

Further, the lower-part terminal electrode lines 414C each extend to the terminal region Ar2 located outside the array region Ar1, and respectively constitute first electrode pads 414P to be connected to first through electrodes 422A described later in the terminal region Ar2.

On the other hand, as shown in FIG. 4, the upper-part electrode 416 has element electrode parts 416A each disposed straddling the plurality of ultrasonic transducers 51 arranged along the Y direction, and common electrode parts 416B (constituting a part of a second electrode line according to the invention) each connecting end parts of the element electrode parts 416A extending in parallel to each other. The element electrode parts 416A each have upper-part electrode main bodies 416C each stacked on the piezoelectric film 415, upper-part electrode lines 416D (constituting a part of the second electrode line according to the invention) each connecting the upper-part electrode main bodies 416C adjacent each other, and upper-part terminal electrodes 416E (constituting a part of the second electrode line according to the invention) extending outward along the Y direction from the respective ultrasonic transducers 51 disposed on the both end parts in the Y direction.

The common electrode parts 416B are disposed respectively in a +Y side end part and a −Y side end part of the array region Ar1. The common electrode part 416B located on the +Y side connects the upper-part terminal electrodes 416E to each other, which extend toward the +Y side from the ultrasonic transducers 51 disposed in the +Y side end part out of the plurality of ultrasonic transducers 51 disposed along the Y direction. The common electrode part 416B located in the −Y side end part connects the upper-part terminal electrodes 416E extending toward the −Y side to each other. Therefore, in the ultrasonic transducers 51 located inside the array region Ar1, the upper-part electrodes 416 are in the same potential. Further, the pair of common electrode parts 416B described above are disposed along the X direction, and the end parts are each drawn from the array region Ar1 to the terminal region Ar2. Further, the common electrode parts 416B constitute second electrode pads 416P to be connected to second through electrodes 422B described later in the terminal region Ar2.

In such an ultrasonic transducer array 50 as described above, there is formed a two-dimensional array structure in which the ultrasonic transducers 51 connected by the lower-part electrode 414 to each other and arranged in the X direction constitute one ultrasonic transducer group 51A, and the plurality of ultrasonic transducer groups 51A is arranged along the Y direction.

Configuration of Sealing Plate 42

The sealing plate 42 is formed to have the same planar shape when viewed from the thickness direction as that of, for example, the element substrate 41, and is formed of a semiconductor substrate such as a silicon substrate, or an insulator substrate. It should be noted that the material and the thickness of the sealing plate 42 affect the frequency characteristics of the ultrasonic transducer 51, and are therefore preferably set based on the central frequency of the ultrasonic wave transmitted/received by the ultrasonic transducer 51.

Further, the sealing plate 42 is provided with a plurality of concave grooves 421, which correspond respectively to the opening parts 411A of the element substrate 41, formed in an array opposed region Ar3 (see FIG. 4) opposed to the array region Ar1 of the element substrate 41. Thus, it results that a gap 421A having a predetermined dimension is provided between the element substrate 41 and the area (inside the opening part 411A) vibrated by the ultrasonic transducer 51 in the vibrating film 412, and the vibration of the vibrating film 412 is prevented from being hindered. Further, it is possible to suppress the problem (cross talk) that the back wave from one ultrasonic transducer 51 enters another ultrasonic transducer 51 adjacent to that ultrasonic transducer 51.

It should be noted that it is also possible that an area (a support part 411B, see FIG. 5) other than the opening parts 411A of the substrate main body part 411 and an area other than the grooves 421 of the sealing plate 42 have contact with, or are bonded to each other.

Further, when the vibrating film 412 vibrates, an ultrasonic wave is also emitted toward the sealing plate 42 side (the rear surface 41A side) as the back wave in addition to the opening part 411A side (the operation surface 41B side). The back wave is reflected by the sealing plate 42, and is then emitted again toward the vibrating film 412 side via the gap 421A. On this occasion, if the phase of the reflected back wave and the phase of the ultrasonic wave emitted from the vibrating film 412 toward the operation surface 41B side are shifted from each other, the ultrasonic wave is attenuated. Therefore, in the present embodiment, the groove depth of each of the concave grooves 421 is set so that the acoustic distance in the gap 421A becomes an odd multiple of a quarter ($\lambda/4$) of the wavelength $\lambda$ of the ultrasonic wave. In other words, the thickness dimensions of the variety of parts of the element substrate 41 and the sealing plate 42 are set taking the wavelength $\lambda$ of the ultrasonic wave emitted from the ultrasonic transducers 51 into consideration.

Further, the sealing plate 42 is provided with the through electrodes 422 (TSV; Through-Silicon Via), which penetrate the sealing plate 42 in the thickness direction, so as to correspond to the respective electrode pads 414P, 416P disposed in the terminal regions Ar2 at positions opposed to the terminal regions Ar2 of the element substrate 41. Specifically, there are disposed the first through electrodes 422A (see FIG. 4) disposed at the positions opposed to the first electrode pads 414P of the element substrate 41, and the second through electrodes 422B (see FIG. 4) disposed at the positions opposed to the second electrode pads 416P.

The first through electrodes 422A are respectively bonded to the first electrode pads 414P with a bonding member 423 having an electrically-conductive property such as solder, and the second through electrodes 422B are respectively bonded to the second electrode pads 416P with the bonding member 423 having an electrically-conductive property such as solder.

Further, the sealing plate 42 is bonded to the element substrate 41 with a bonding film, an adhesive, or the like in an outer peripheral region Ar4 other than the array region Ar1 and the terminal regions Ar2 of the element substrate 41. Thus, it becomes possible for the sealing plate 42 to increase the substrate strength of the element substrate 41.

Configuration of Acoustic Matching Layer 43 and Acoustic Lens 44

As shown in FIG. 5, the acoustic matching layer 43 is disposed on the operation surface 41B of the element substrate 41. Specifically, the acoustic matching layer 43 is formed so as to fill in the opening parts 411A of the element substrate 41, and to have a predetermined thickness dimension from the operation surface 41B side of the substrate main body part 411.

The acoustic lens 44 is disposed on the acoustic matching layer 43, and as shown in FIG. 1, exposed to the outside from the sensor window 21B of the housing 21.

The acoustic matching layer 43 and the acoustic lens 44 efficiently propagate the ultrasonic wave emitted from the ultrasonic transducers 51 to the living body as the measurement object, and further propagate the ultrasonic wave, which has been reflected in the living body, to the ultrasonic transducers 51 with efficiency. Therefore, the acoustic matching layer 43 and the acoustic lens 44 are set to have an acoustic impedance intermediate between the acoustic impedance of the ultrasonic transducers 51 of the element substrate 41 and the acoustic impedance of the living body.

Configuration of Wiring Board 23

As shown in FIG. 5, the wiring board 23 has the wiring terminal parts 231 corresponding respectively to the through electrodes 422 of the sealing plate 42, and the through electrodes 422 are bonded to the wiring terminal parts 231 with the electrically-conductive bonding member 232 such as solder.

Further, the wiring board 23 is provided with a driver circuit for driving the ultrasonic device 22, and so on. Specifically, as shown in FIG. 2, the wiring board 23 is provided with a selection circuit 233, a transmission circuit 234, a reception circuit 235, a connector part 236 (see FIG. 3), and so on.

The selection circuit 233 switches between transmission connection of connecting the ultrasonic device 22 and the transmission circuit 234 to each other, and reception connection of connecting the ultrasonic device 22 and the reception circuit 235 to each other based on the control of the control device 10.

The transmission circuit 234 outputs a transmission signal, which represents the fact that the ultrasonic device 22 is made to transmit the ultrasonic wave via the selection circuit 233 when switching to the transmission connection is made due to the control of the control device 10.

The reception circuit 235 outputs a reception signal, which is input from the ultrasonic device 22, to the control device 10 via the selection circuit 233 when switching to the reception connection is made due to the control of the control device 10. The reception circuit 235 is configured including, for example, a low-noise amplifier circuit, a voltage-controlled attenuator, a programmable-gain amplifier, a low-pass filter, and an A/D converter, and performs a variety of signal processing such as conversion of the reception signal to a digital signal, elimination of a noise component, and amplification to a desired signal level, and then outputs the reception signal thus processed to the control device 10.

The connector part 236 is connected to the transmission circuit 234 and the reception circuit 235. Further, the cable 3 is connected to the connector part 236, and as described above, the cable 3 is drawn through the through hole 21C of the housing 21 and is then connected to the control device 10.

Method of Mounting Ultrasonic Device 22 on Wiring Board 23

Figure 6A:
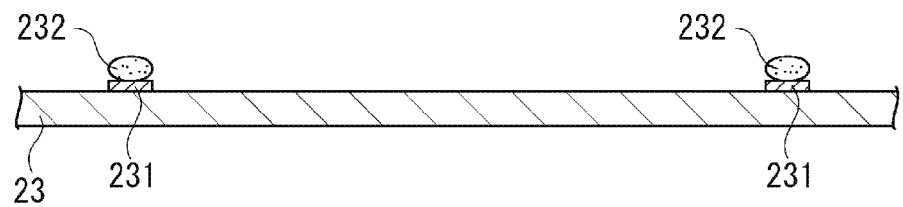
FIGS. 6A through 6C are diagrams showing a method of mounting the ultrasonic device according to the embodiment on a wiring board.
Figure 6B:
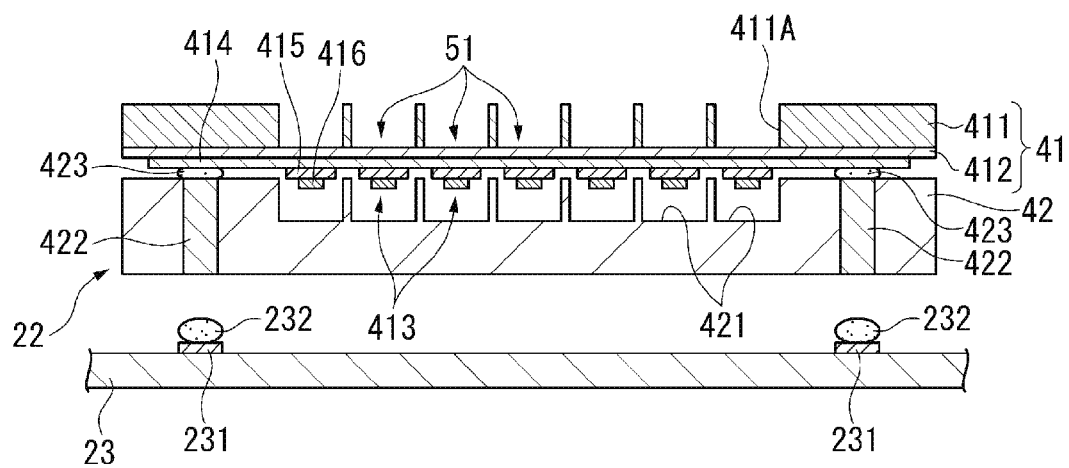
Figure 6C:
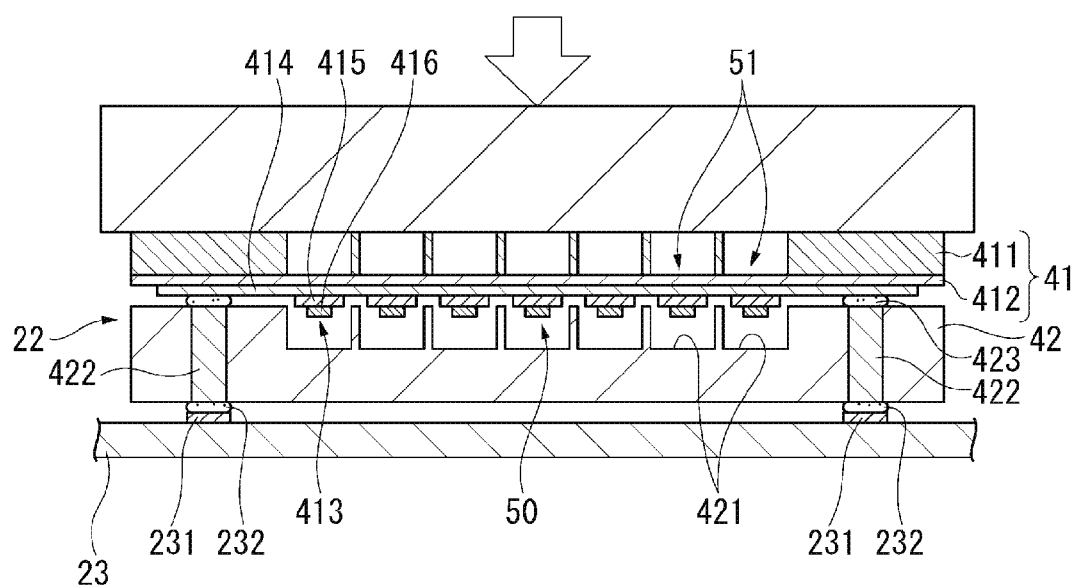

FIGS. 6A through 6C are diagrams showing a method of mounting the ultrasonic device 22 according to the present embodiment on the wiring board 23.

As described above, in the present embodiment, in the ultrasonic device 22, the sealing plate 42 is bonded to the element substrate 41, and the through electrodes 422 are disposed at the positions of the sealing plate 42 opposed to the respective electrode pads 414P, 416P of the element substrate 41, and are each bonded thereto with the bonding member 423.

Therefore, in the connection between the ultrasonic device 22 and the wiring board 23, firstly, the electrically-conductive bonding member 232 such as solder is provided to each of the wiring terminal parts 231 disposed at the positions opposed to the respective through electrodes 422 of the wiring board 23 as shown in FIG. 6A.

Subsequently, as shown in FIGS. 6B and 6C, the ultrasonic device 22 is to overlap the wiring board 23 from the normal direction thereof, and is then pressed by a pressing member or the like. Thus, the through electrodes 422 and the wiring terminal parts 231 are bonded to each other with the bonding member 232, and thus, the ultrasonic device 22 can easily be mounted on the wiring board 23.

Figure 7:
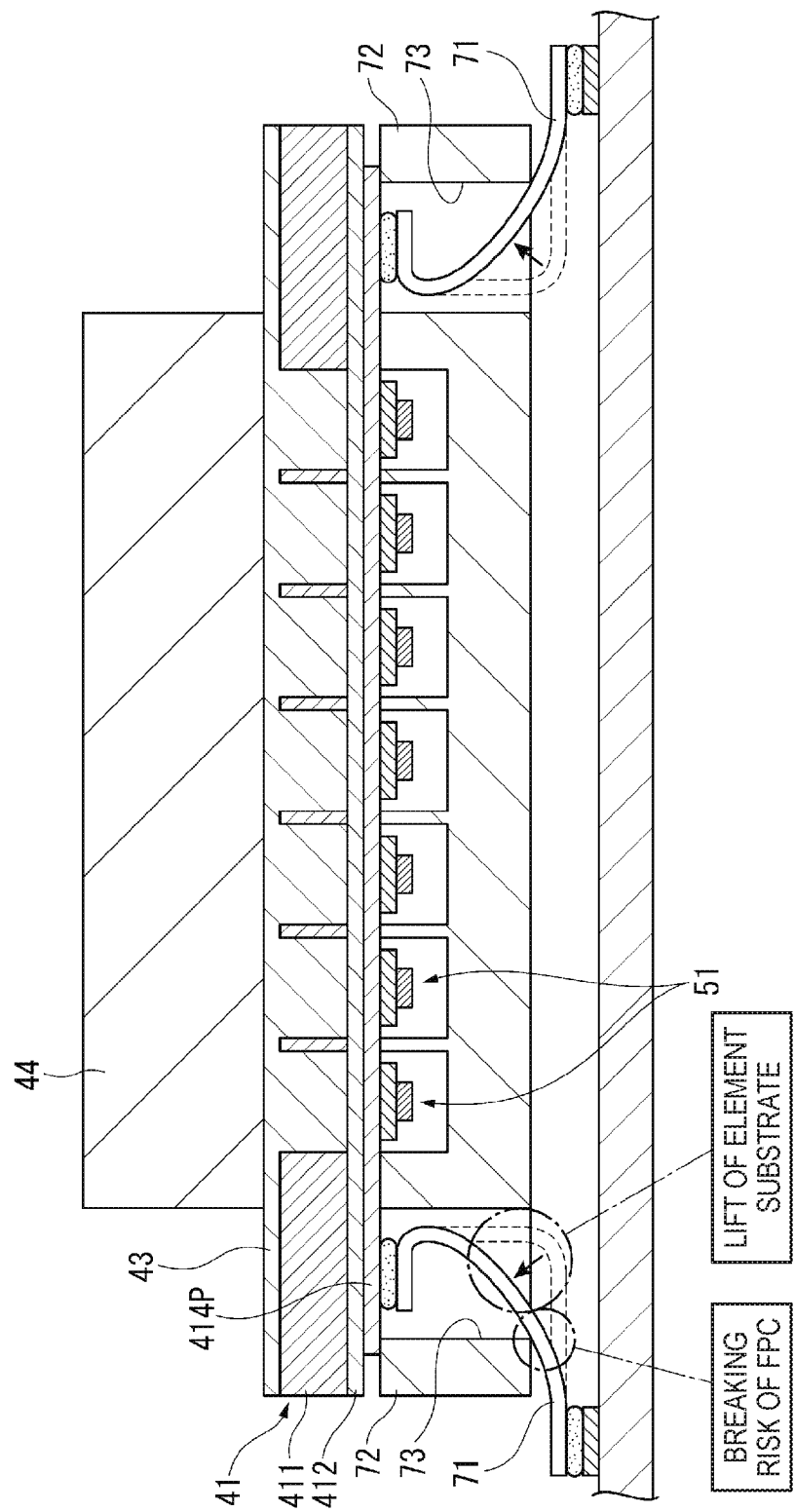
FIG. 7 is a cross-sectional view showing a configuration example of a related-art ultrasonic device.

In such face-down mounting, braking of the wiring due to the contact between an FPC 71 and a corner part of an opening 73 in a sealing plate 72 as in a related-art example shown in FIG. 7 does not occur, and the wiring reliability is enhanced. Further, since the lift of the ultrasonic device due to the tension of the FPC 71 does not occur, it is possible to accurately transmit the ultrasonic wave from the ultrasonic transducer array 50 toward a desired direction, and further, it is possible to accurately receive the ultrasonic wave from the desired direction.

Configuration of Control Device 10

As shown in FIG. 2, the control device 10 is configured including, for example, an operation section 11, a display section 12, a storage section 13, and an arithmetic section 14. As the control device 10, there can be used a terminal device such as a tablet terminal, a smartphone, or a personal computer, and the control device 10 can also be a dedicated terminal device for operating the ultrasonic probe 2.

The operation section 11 is a user interface (UI) for the user to operate the ultrasonic measurement apparatus 1, and can be formed of, for example, a touch panel or operation buttons disposed on the display section 12, a keyboard, or a mouse.

The display section 12 is formed of, for example, a liquid crystal display, and displays an image.

The storage section 13 stores a variety of programs and a variety of data for controlling the ultrasonic measurement apparatus 1.

The arithmetic section 14 is formed of an arithmetic circuit such as a central processing unit (CPU), and a storage circuit such as a memory. Further, the arithmetic section 14 retrieves and then executes the variety of programs stored in the storage section 13 to perform control of a process of generating and outputting the transmission signal on the transmission circuit 234, and to perform control of frequency setting, gain setting, and so on of the reception signal on the reception circuit 235.

Functions and Advantages of Present Embodiment

In the present embodiment, the ultrasonic transducers 51 constituting the ultrasonic transducer array 50 and the electrode lines (the lower-part electrode lines 414B, the lower-part terminal electrode lines 414C, the upper-part electrode lines 416D, and the upper-part terminal electrodes 416E) to be connected to the ultrasonic transducers 51 are disposed on the rear surface 41A side of the element substrate 41. Further, the sealing plate 42 is disposed to the rear surface 41A of the element substrate 41, and the sealing plate 42 is provided with the through electrodes 422 to electrically be connected to the respective electrode pads 414P, 416P as the end parts of the electrode lines described above at the positions opposed to the terminal regions Ar2.

In such a configuration, since there is provided the configuration in which the ultrasonic transducer array 50 and the respective electrode lines are disposed on the rear surface 41A side of the element substrate 41, which is the opposite side to the surface having contact with the living body in the ultrasonic probe 2, even if a liquid such as a gel intervenes between the ultrasonic probe 2 and the living body, and the liquid infiltrates from a gap of the sensor window 21B, the liquid does not adhere to the ultrasonic transducers 51 or the electrode lines, and thus, a malfunction such as a failure or measurement error can be inhibited.

Further, since the sealing plate 42 is disposed, even in the case in which the element substrate 41 is thin, the strength of the element substrate 41 can be reinforced, and breakage due to an impact or the like can be inhibited. Further, since the through electrodes 422 are disposed so as to be opposed to the terminal regions Ar2 of the sealing plate 42, the electrode pads 414P, 416P of the element substrate 41 and the wiring terminal parts 231 of the wiring board 23 can easily be connected to each other using the face-down mounting. Therefore, compared to the configuration using the FPC as in the related art, the transmission/reception accuracy of the ultrasonic wave can be improved, and at the same time, the wiring reliability can also be improved.

In the present embodiment, the element substrate 41 has the opening parts 411A corresponding respectively to the ultrasonic transducers 51, the rear surface 41A side of the opening part 411A is closed by the vibrating film 412, and the piezoelectric element 413 is disposed on the rear surface 41A side of the vibrating film 412.

In such a configuration, by driving the piezoelectric elements 413 to vibrate the vibrating film 412 having the thin-film shape, it is possible to emit the ultrasonic wave, and further, by detecting the vibration of the vibrating film 412 with the piezoelectric elements 413, it is possible to receive the ultrasonic wave. Further, since the vibrating film 412 is disposed on the rear surface 41A side of the opening parts 411A, compared to the configuration in which, for example, the vibrating film 412 is disposed on the operation surface 41B side of the opening parts 411A, and the piezoelectric element 413 is disposed inside each of the opening parts 411A, it becomes easy to form the piezoelectric elements 413, and further, since the electrode lines (the lower-part electrode lines 414B, the lower-part terminal electrode lines 414C, the upper-part electrode main bodies 416C, and the upper-part electrode lines 416D) drawn from the respective piezoelectric elements 413 can be formed on the flat vibrating film 412, breaking of these electrode lines can be inhibited.

In the present embodiment, in the ultrasonic transducer array 50, the plurality of ultrasonic transducers 51 disposed along the X direction constitutes the ultrasonic transducer group 51A, and in the ultrasonic transducers 51 belonging to the ultrasonic transducer group 51A, the lower-part electrode 414 is used in common, and the lower-part electrode main bodies 414A of the ultrasonic transducers 51 adjacent to each other are connected to each other by the lower-part electrode line 414B. Further, the ultrasonic transducer 51 located at the end part of each of the ultrasonic transducer groups 51A is extracted to the terminal region Ar2 by the lower-part terminal electrode line 414C, and is then connected from the first electrode pad 414P to the wiring board via the first through electrode 422A. Further, the upper-part electrode 416 is provided with the element electrode parts 416A arranged along the Y direction and the common electrode parts 416B disposed on the both end parts of the element electrode parts 416A to connect the element electrode parts 416A adjacent to each other, and the common electrode parts 416B are each drawn to the terminal regions Ar2, and are connected from the second electrode pads 416P to the wiring board 23 via the second through electrodes 422B, respectively. Therefore, the upper-part electrodes 416 of all of the ultrasonic transducers 51 in the ultrasonic transducer array 50 become common (the same in potential).

In such a configuration, in the wiring board 23, the wiring terminals 231 to be connected to the second through electrodes 422B are connected to a ground circuit or the like to thereby be set to a common potential (e.g., 0 potential). Meanwhile, in the wiring substrate 23, the wiring terminal parts 231 to be connected to the first through electrodes 422A are connected to the transmission circuit 234 or the reception circuit 235 via the selection circuit 233. When transmitting the ultrasonic wave, the transmission signal is applied from the transmission circuit 234, and further, when receiving the ultrasonic wave, the detection signal can be input to the reception circuit 235. Thus, it is possible to treat the ultrasonic transducer array 50 as the one-dimensional array structure.

Modified Examples

It should be noted that the invention is not limited to each of the embodiments described above, but includes modifications and improvements within a range where the advantages of the invention can be achieved, and configurations, which can be obtained by, for example, arbitrarily combining the embodiments.

Although in the embodiment, there is illustrated the one-dimensional array structure in which the plurality of ultrasonic transducers 51 arranged in the X direction constitute the ultrasonic transducer group 51A, and the ultrasonic transducer groups 51A are arranged in the Y direction in the ultrasonic transducer array 50, the invention is not limited to this configuration. It is also possible that, for example, the lower-part electrodes 414 of the respective ultrasonic transducers 51 are individually drawn to the terminal region Ar2, and then individually connected to the wiring board 23 via the through electrodes 422, respectively. In this case, it becomes possible to individually drive the ultrasonic transducers 51, and it becomes possible to drive the ultrasonic transducer array 50 as the two-dimensional array.

Although in the embodiment described above, there is illustrated the configuration in which the upper-part electrodes 416 of all of the ultrasonic transducers 51 constituting the ultrasonic transducer array 50 are connected to each other by the common electrode parts 415B, the invention is not limited to this configuration. It is also possible that, for example, the upper-part electrodes 416 of the respective ultrasonic transducers 51 are individually drawn to the terminal regions Ar2, and are individually connected to the through electrodes 422 (the second through electrodes 422B).

Further, similarly to the lower-part electrodes 414, it is also possible to adopt the configuration in which the upper-part electrodes 416 are connected to each other in the ultrasonic transducers 51 constituting the ultrasonic transducer group 51A, and then drawn to the terminal regions Ar2.

Although in the embodiment described above, there is adopted the configuration in which the terminal regions Ar2 are disposed on the −X side and the +X side of the array region Ar1 in which the ultrasonic transducer array 50 is disposed in the element substrate 41, it is also possible to adopt a configuration in which, for example, the terminal region Ar2 is disposed only either one of the −X side and the +X side. Further, it is also possible to dispose the terminal regions Ar2 on the ±Y sides of the ultrasonic transducer array 50, and dispose the through electrodes 422 to the sealing plate 42 so as to correspond to the electrode lines drawn to the terminal regions Ar2.

Although there is described the configuration for measuring the internal tomographic structure of the living body as an example of the ultrasonic measurement apparatus 1, the invention can also be used as other devices such as a measuring instrument for inspecting the internal structure of a concrete such as a concrete building.

Further, although the ultrasonic measurement apparatus 1 provided with the ultrasonic device 22 is illustrated, the invention can also be applied to other electronic apparatuses. The invention can be used for, for example, an ultrasonic washing machine for feeding the ultrasonic wave to a cleansing object to perform ultrasonic cleansing on the cleansing object.

Figure 8:
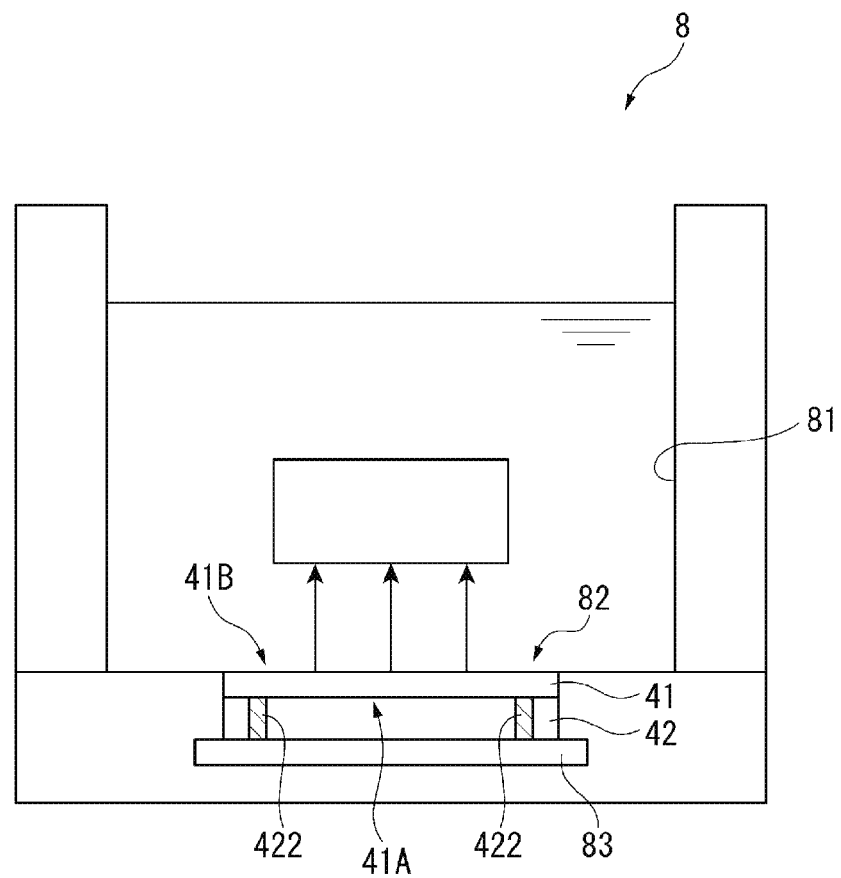
FIG. 8 is a diagram showing an example of an electronic apparatus according to another embodiment of the invention.

FIG. 8 is a diagram showing a general configuration of the ultrasonic washing machine.

The ultrasonic washing machine 8 shown in FIG. 8 is provided with a washing tank 81, and an ultrasonic module 82 disposed on, for example, a bottom surface of the washing tank 81.

The ultrasonic module 82 is provided with the ultrasonic device 22 substantially the same as that of the embodiment described above, and a wiring board 83 for controlling the ultrasonic device 22. Specifically, the ultrasonic device 22 is provided with the element substrate 41 having an operation surface 41B facing the inner surface of the washing tank 81, and the sealing plate 42 disposed on the rear surface 41A side of the element substrate 41, and is provided with the ultrasonic transducer array 50 (not shown in FIG. 8) constituted by the plurality of ultrasonic transducers 51 (not shown in FIG. 8), and electrode lines drawn to the outside of the array region Ar1 (not shown in FIG. 8) of the ultrasonic transducer array 50 on the rear surface 41A side of the element substrate 41. Further, the electrode lines are connected to the through electrodes 422 provided to the sealing plate 42 in the terminal regions Ar2 located outside the array region Ar1, and the through electrodes 422 are electrically connected to the wiring terminal parts (not shown) disposed on the wiring board 83, respectively.

In such a configuration, the ultrasonic device 22 can easily be mounted on the wiring board 83 using the face-down mounting. Further, since the operation surface 41B side of the element substrate 41 faces the washing tank 81 side, the waterproof property of the ultrasonic transducers 51 and the electrode lines disposed on the rear surface 41A side can be enhanced.

Although in the embodiment described above, there is adopted the configuration in which the opening parts 411A are disposed in the element substrate 41, it is also possible to adopt a configuration in which, for example, the opening parts 411A are not disposed in the element substrate 41, the ultrasonic transducers 51 each vibrate the element substrate 41 itself to emit the ultrasonic wave, and detect the reception of the ultrasonic wave based on the vibration of the element substrate 41.

Further, although there is illustrated the configuration of disposing the vibrating film 412 on the rear surface 41A side of the opening parts 411A, it is also possible to adopt a configuration in which, for example, the vibrating film 412 is disposed on the operation surface 41B side of the opening parts 411A, and the piezoelectric element 413 constituting the ultrasonic transducer 51 is disposed on the rear surface 41A side of the vibrating film 412.

Although in the embodiment described above, there is adopted the configuration in which the vibrating film 412 is disposed on the rear surface 41A side of the substrate main body part 411 provided with the opening parts 411A, the invention is not limited to this configuration. It is also possible to adopt a configuration in which, for example, a plurality of concave grooves corresponding respectively to the ultrasonic transducers 51 is disposed on the operation surface 41B side of the substrate main body part 411, and the bottom surface of each of the concave grooves is used as the vibrating film.

Besides the above, specific structures to be adopted when implementing the invention can be configured by arbitrarily combining the embodiments and the modified examples described above, or can arbitrarily be replaced with other structures and so on within the range in which the advantages of the invention can be achieved.

The entire disclosure of Japanese Patent Application No. 2015-147109 filed on Jul. 24, 2015 is expressly incorporated by reference herein.

What is claimed is:

1. An ultrasonic device comprising:
    an element substrate having a first surface and a second surface located on an opposite side to the first surface;
    an ultrasonic transducer array disposed on the first surface of the element substrate, the ultrasonic transducer array having a plurality of ultrasonic transducers arranged in an array, each of the plurality of ultrasonic transducers being configured with a lower electrode, a piezoelectric film, and an upper electrode, the piezoelectric film being sandwiched between the lower and upper electrodes, the lower electrode being closer to the first surface of the element substrate than the upper electrode;
    at least one electrode line connected to the lower electrode of one of the plurality of ultrasonic transducers, the at least one electrode line extending to a periphery of the ultrasonic transducer array in a plan view so that a distal end of the at least one electrode line is located next to an edge of the element substrate;
    a sealing plate having third and fourth surfaces opposite to each other, the third surface being bonded to the first surface of the element substrate, the sealing plate having a through hole in a thickness direction of the sealing plate, the through hole being located next to an edge of the sealing plate in the plan view;
    a through electrode disposed inside of the through hole of the sealing plate; and
    a circuit board disposed to face the fourth surface of the sealing plate, the circuit board having a terminal pad thereon,
    wherein the through electrode is physically and electrically connected between the at least one electrode line and the terminal pad of the circuit board, and
    the through electrode is laterally shifted away from the piezoelectric films of the plurality of ultrasonic transducers without overlapping with the piezoelectric films in the plan view.

2. The ultrasonic device according to claim 1, wherein the element substrate is provided with a plurality of openings corresponding respectively to the plurality of ultrasonic transducers, and a vibrating film closes the plurality of openings.

3. The ultrasonic device according to claim 2, wherein the vibrating film closes plurality of openings located at a side of first surface of the element substrate.

4. The ultrasonic device according to claim 1, further comprising:
    another electrode line connected to the upper electrode of one of the plurality of ultrasonic transducers,
    wherein the sealing plate has another through hole in the thickness direction of the sealing plate, and the another through hole is located next to another edge of the sealing plate in the plan view,
    another through electrode is disposed inside of the another through hole of the sealing plate, and the circuit board has another terminal pad thereon, and
    the another through electrode is physically and electrically connected between the another electrode line and the another terminal pad of the circuit board.

5. The ultrasonic device according to claim 4, wherein some of the plurality of the ultrasonic transducers are arranged along a first direction so as to constitute an ultrasonic transducer group, and a plurality of the ultrasonic transducer groups is arranged along a second direction crossing the first direction,
    the at least one electrode lines are connected respectively to the lower electrodes of the ultrasonic transducers belonging to the ultrasonic transducer group so that the ultrasonic transducers belonging to the ultrasonic transducer group are electrically connected to each other, and
    the another electrode lines are connected respectively to the upper electrodes of the ultrasonic transducers belonging to the ultrasonic transducer group so that the ultrasonic transducers belonging to the ultrasonic transducer group are electrically connected to each other.

6. An electronic apparatus comprising:
    an element substrate having a first surface and a second surface located on an opposite side to the first surface;
    an ultrasonic transducer array disposed on the first surface of the element substrate, and having a plurality of ultrasonic transducers arranged in an array, each of the plurality of ultrasonic transducers being configured with a lower electrode, a piezoelectric film, and an upper electrode, the piezoelectric film being sandwiched between the lower and upper electrodes, the lower electrode being closer to the first surface of the element substrate than the upper electrode;
    at least one electrode line connected to the lower electrode of one of the plurality of ultrasonic transducers, the at least one electrode line extending to a periphery of the ultrasonic transducer array in a plan view so that a distal end of the at least one electrode line is located next to an edge of the element substrate;
    a sealing plate having third and fourth surfaces opposite to each other, the third surface being bonded to the first surface of the element substrate, the sealing plate having a through hole in a thickness direction of the sealing plate, the through hole being located next to an edge of the sealing plate in the plan view;
    a through electrode disposed inside of the through hole of the sealing plate;
    a wiring board disposed to face the fourth surface of the sealing plate, the wiring board having a terminal pad thereon; and
    a control section configured to control the plurality of ultrasonic transducers, wherein the through electrode is physically and electrically connected between the at least one electrode line and the terminal pad of the wiring board, and the through electrode is laterally shifted away from the piezoelectric films of the plurality of ultrasonic transducers without overlapping with the piezoelectric films in the plan view.

7. An ultrasonic measurement apparatus comprising:

an element substrate having a first surface and a second surface located on an opposite side to the first surface;

an ultrasonic transducer array disposed on the first surface of the element substrate, and having a plurality of ultrasonic transducers arranged in an array;

at least one electrode line connected to the ultrasonic transducer in the first surface of the element substrate, and drawn outside the ultrasonic transducer array in a planar view of the element substrate viewed from a normal direction;

a sealing plate bonded to the first surface of the element substrate;

at least one through electrode, which is disposed so as to penetrate the sealing plate in a thickness direction and is connected to a part of the electrode line at a position, which is outside an array opposed region opposed to the ultrasonic transducer array of the sealing plate in the planar view and is opposed to the part of the electrode line;

a wiring board provided with at least one terminal part to be connected to the through electrode; and a measurement control section adapted to control transmission of an ultrasonic wave from the ultrasonic transducer array and reception of the ultrasonic wave reflected to measure a measurement target based on transmission/reception timing of the ultrasonic wave.

\* \* \* \* \*